(12) United States Patent
Kida et al.

(10) Patent No.: US 9,013,697 B2
(45) Date of Patent: Apr. 21, 2015

(54) BAND DETECTION SENSOR AND DETECTION METHOD THEREFOR

(71) Applicant: Japan Tobacco Inc., Tokyo (JP)

(72) Inventors: Shinzo Kida, Tokyo (JP); Takafumi Izumiya, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 14/178,438

(22) Filed: Feb. 12, 2014

(65) Prior Publication Data

US 2014/0168653 A1 Jun. 19, 2014

Related U.S. Application Data

(63) Continuation of application No. PCT/JP2011/077042, filed on Nov. 24, 2011.

(51) Int. Cl.
| | |
|---|---|
| *G01N 21/84* | (2006.01) |
| *G01N 21/55* | (2014.01) |
| *A24D 1/02* | (2006.01) |
| *A24C 5/34* | (2006.01) |
| *D21H 27/00* | (2006.01) |

(52) U.S. Cl.
CPC ............... *G01N 21/55* (2013.01); *A24D 1/025* (2013.01); *A24C 5/3412* (2013.01); *D21H 27/00* (2013.01)

(58) Field of Classification Search
USPC ............... 356/429–431, 237.1–237.5, 448; 250/559.01, 559.15, 223 R, 559.4, 250/559.45, 559.46; 209/579, 585
See application file for complete search history.

(56) References Cited

U.S. PATENT DOCUMENTS

| | | | |
|---|---|---|---|
| 5,127,737 A * | 7/1992 | Neri .............................. | 356/394 |
| 6,020,969 A | 2/2000 | Struckhoff et al. | |
| 6,097,482 A * | 8/2000 | Smith et al. ................. | 356/237.1 |
| 6,407,807 B1 * | 6/2002 | Focke et al. ................. | 356/237.1 |
| 2005/0230647 A1 * | 10/2005 | Gotoh et al. ............. | 250/559.45 |
| 2013/0242292 A1 * | 9/2013 | Kida et al. ................. | 356/237.2 |

FOREIGN PATENT DOCUMENTS

| | | |
|---|---|---|
| JP | 1-57949 B2 | 12/1989 |
| JP | 2006-90802 A | 4/2006 |
| JP | 3980267 B2 | 9/2007 |
| JP | 2010-531151 A | 9/2010 |
| WO | WO 99/02051 A1 | 1/1999 |
| WO | WO 2009/001223 A2 | 12/2008 |

* cited by examiner

*Primary Examiner* — Hoa Pham
(74) *Attorney, Agent, or Firm* — Birch, Stewart, Kolasch & Birch, LLP (57) ABSTRACT

A band detection sensor includes LEDs configured to radiate detection light onto one side of a web, photodiodes configured to receive the detection light reflected by the web and output a detection signal corresponding to the detection light, and a discrimination section configured to discriminate bands on the web on the basis of the detection signal from the photodiodes, wherein the discrimination section includes a rise discriminating criterion indicating a rate of rise of the detection signal and generates a band signal indicative of the presence of a band when change of the detection signal fulfills the rise discriminating criterion.

9 Claims, 11 Drawing Sheets

BAND DETECTION SENSOR AND DETECTION METHOD THEREFOR

CROSS REFERENCE TO RELATED APPLICATIONS

This application is a continuation application of PCT International Application No. PCT/JP2011/077042 filed on Nov. 24, 2011, which is hereby expressly incorporated by reference into the present application.

TECHNICAL FIELD

The present invention relates to a band detection sensor for detecting bands formed on a web while the web is traveling, and a detection method employed in the band detection sensor.

BACKGROUND ART

This type of band detection sensor includes a light emitter for radiating detection light onto a traveling web, a light receiver for receiving the detection light reflected by the web and outputting a detection signal corresponding to the intensity of the detection light, and a discrimination unit for discriminating the presence of bands on the web on the basis of the detection signal from the light receiver (cf. Patent Document 1). Specifically, the discrimination unit compares an average peak value of the detection signal with a threshold value, and generates a band signal indicative of the presence of a band if the average peak value exceeds the threshold value.

CITATION LIST

Patent Literature

Patent Document 1: Japanese Patent No. 3980267 (JP 3980267 B2)

SUMMARY OF INVENTION

Technical Problem

In the case of the band detection sensor disclosed in Patent Document 1, the threshold value is a fixed value expressed as a percentage of the average peak value. Thus, if the web is wrinkled or deformed wavily as a result of the formation of bands, it is possible that the average peak value of the detection signal derived from a region of the web other than the bands, that is, a non-banded region, will exceed the threshold value. Consequently, the band detection sensor of Patent Document 1 is liable to cause false detection of bands.

An object of the present invention is therefore to provide a band detection sensor and a detection method therefor whereby even if a web is wrinkled or deformed wavily, false detection of bands attributable to such wrinkling or deformation can be prevented, so that the bands can be detected with high detection accuracy, compared with conventional techniques.

Solution to Problem

To achieve the above object, the present invention provides a band detection sensor for detecting bands arranged on one side of a web and spaced from each other in a longitudinal direction of the web, comprising: a light emitter arranged at a location along a travel path of the web and configured to radiate detection light onto the one side of the web; a light receiver arranged at a location along the travel path at a distance from the light emitter along the travel path, the light receiver being configured to receive the detection light reflected by the web and output a detection signal corresponding to intensity of the received detection light; and a band discriminator configured to discriminate the bands on the web on the basis of the detection signal from the light receiver, wherein the band discriminator includes a rise discriminating criterion indicating a rate of rise of the detection signal and generates a band signal indicative of presence of the band when change of the detection signal fulfills the rise discriminating criterion.

With the above band detection sensor, the band discriminator generates a band signal when change of the detection signal fulfills the rise discriminating criterion, and thus the band signal accurately indicates the presence of a band irrespective of the surface condition (wrinkles or undulations) of the web. Consequently, the band detection sensor can detect only the bands with high accuracy.

The detection light is preferably invisible light, that is, near-infrared light. In this case, the band detection sensor can detect bands without being adversely affected by external light such as light from lighting equipment.

Preferably, the angle between the optical axis of the light emitter and the one side of the web is 30 degrees or less. In this case, since a large incidence angle is secured for the detection light incident on the web, transmission of the detection light through the web is restrained, with the result that the detection light reflected from the web is increased in intensity.

Specifically, the rise discriminating criterion is represented by two positions on the web spaced from each other in the longitudinal direction of the web and a level difference between the detection signals obtained at the two positions. Further, the band discriminator preferably discriminates the bands on the web on the basis of a moving average value calculated from a predetermined number of the detection signals and the rise discriminating criterion.

The band discriminator may further include a fall discriminating criterion indicating a rate of fall of the detection signal.

Further, where the bands are arranged on the web with a fixed pitch, the band detection sensor may further comprise a band lack discriminator configured to discriminate lack of the band, and the band lack discriminator outputs a band lack signal when a predetermined threshold value is reached by a counter value which is incremented while being reset each time the band signal is output or output of the band signal is stopped. In this case, the band lack signal accurately indicates the lack of a band.

The present invention also provides a detection method for detecting the bands, and details of the detection method and band detection sensor will become apparent from the following description when taken in conjunction with the accompanying drawings.

Advantageous Effects of Invention

With the band detection sensor and detection method of the present invention, the band signal indicative of the presence of a band is output when change of the detection signal fulfills the rise discriminating criterion, and accordingly, even if the web is wrinkled or wavily deformed, the bands on the web can be accurately detected regardless of such wrinkling or wavy deformation.

DESCRIPTION OF EMBODIMENTS

Figure 1:
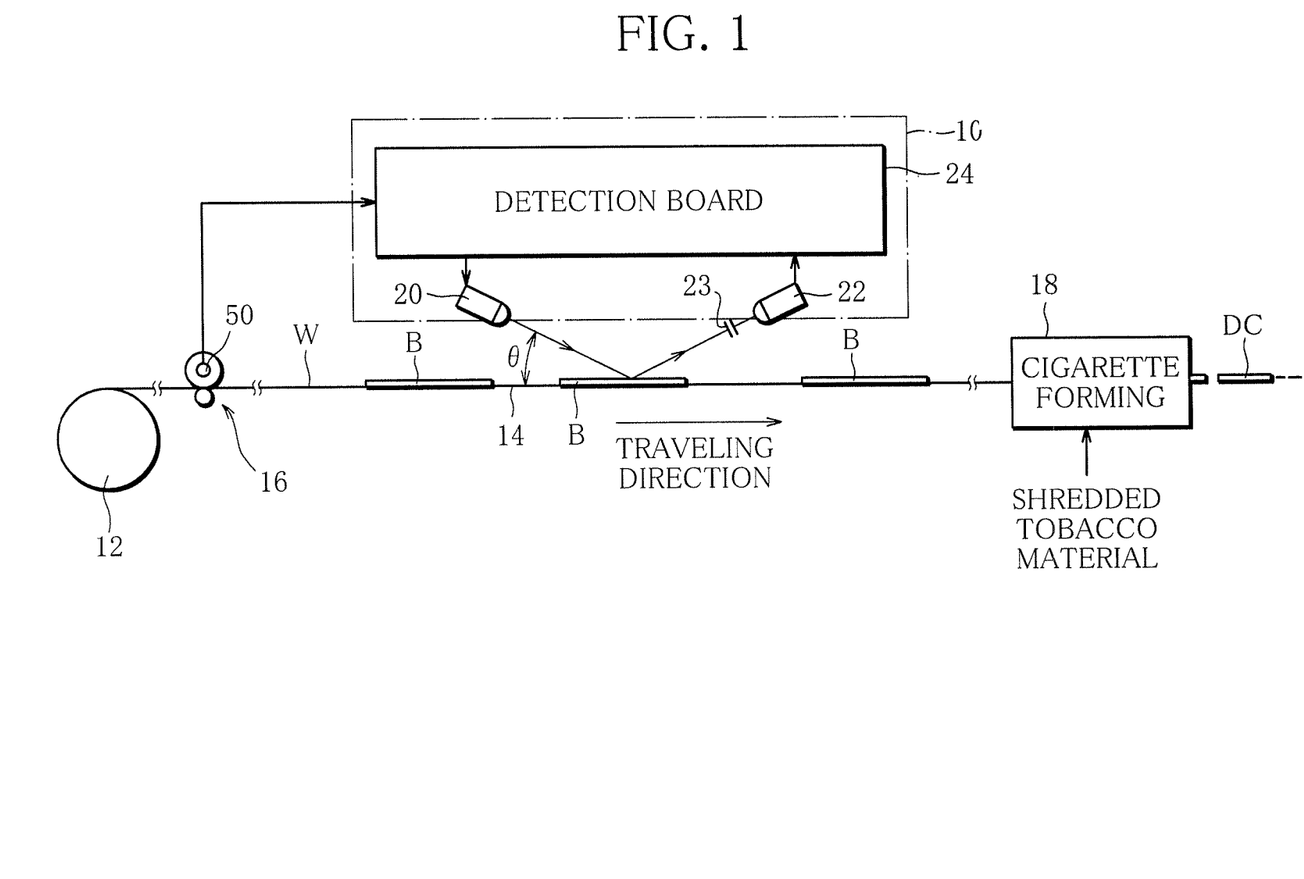
FIG. 1 schematically illustrates a band detection sensor of an embodiment, applied to a cigarette manufacturing machine.

Referring to FIG. 1, a band detection sensor 10 according to an embodiment is applied to a cigarette manufacturing machine. The cigarette manufacturing machine is provided with a web roll 12, and a web W is fed from the web roll 12 to a cigarette forming device 18 along a travel path 14.

Specifically, a feed roller unit 16 is disposed in the travel path 14 and feeds the web W from the web roll 12 toward the forming device 18 at a fixed traveling speed.

The web W has numerous bands B formed thereon. The bands B are spaced from each other with a fixed pitch in a longitudinal direction of the web W and extend in a width direction of the web W. The bands B are formed by applying a combustion inhibitor in liquid form to one side of the web W.

The forming device 18 receives shredded tobacco material along with the web W. In the forming device 18, the shredded tobacco material is continuously wrapped in the web W to form a tobacco rod. The formed tobacco rod is cut to a predetermined length to obtain double cigarettes DC. Each double cigarette DC has a double-length paper wrapper formed of a portion of the web W.

Subsequently, the double cigarettes DC are supplied, together with filter rods, to a filter attachment machine. The filter attachment machine forms filter cigarettes FC, as exemplified in FIG. 2, from the double cigarettes DC and the filter rods.

Figure 2:
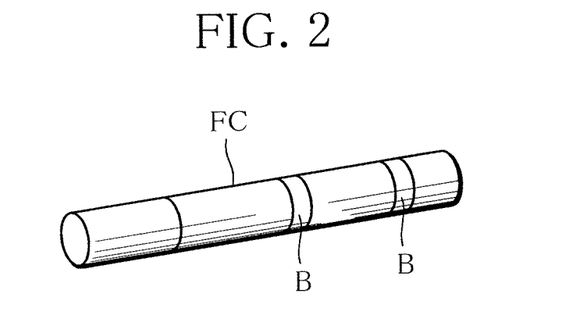
FIG. 2 is a perspective view of a filter cigarette produced using the manufacturing machine of FIG. 1.

Specifically, in the filter attachment machine, each double cigarette DC is cut into two cigarettes, and each filter rod is also cut into a plurality of filter plugs. Then, with one filter plug placed between two cigarettes, the cigarettes and the filter plug are connected together by being wound with tipping paper, thus forming a double filter cigarette. The double filter cigarette is cut into two equal parts, whereby two filter cigarettes FC are obtained from one double filter cigarette.

The paper wrapper of each filter cigarette FC has two bands B, and the bands B impart low ignition propensity to the filter cigarette FC. The filter rods and the filter attachment machine are not illustrated in FIG. 1.

As is clear from FIG. 1, the aforementioned band detection sensor 10 is arranged between the feed roller unit 16 and the forming device 18, and carries out a method of detecting the bands B in the manner described below. The band detection sensor 10 includes a plurality of light emitting diodes (LEDs) 20 as a light emitter, a plurality of photodiodes 22 as a light receiver, and a detection board 24.

The LEDs 20 radiate detection light onto one side of the web W over its entire width (radiation process). Specifically, the detection light is invisible light having a wavelength selected from a near-infrared wavelength region of 750 nm to 1500 nm, for example, a wavelength of 950 nm, and the angle between the optical axis of the detection light and the irradiated side of the web W is set to 30 degrees or less.

The photodiodes 22 are located downstream of the LEDs 20 as viewed in the traveling direction of the web W. The photodiodes 22 receive the detection light reflected from the one side of the web W, that is, from the bands B or non-banded regions other than the bands B, and generate an electrical detection signal corresponding to the received detection light (output process). In this embodiment, the band detection sensor 10 further includes an optical filter 23 arranged just in front of the photodiodes 22, and the optical filter 23 cuts off light having wavelengths shorter than 750 nm, namely, visible light.

The LEDs 20 and the photodiodes 22 are electrically connected to the detection board 24. The detection board 24 adjusts the amount of the detection light radiated from the LEDs 20 as well as the light receiving sensitivity of the photodiodes 22, and detects the bands B and the like of the web W on the basis of the detection signal, as described later.

The detection board 24 is what is called a single-board computer and includes a circuit board and components mounted on the circuit board, such as microprocessors, custom LSI, memory, and input/output interfaces. In the following, functionality of the detection board 24, instead of specific configuration of the detection board 24, will be described in detail with reference to the functional block diagram of FIG. 3.

Figure 3:
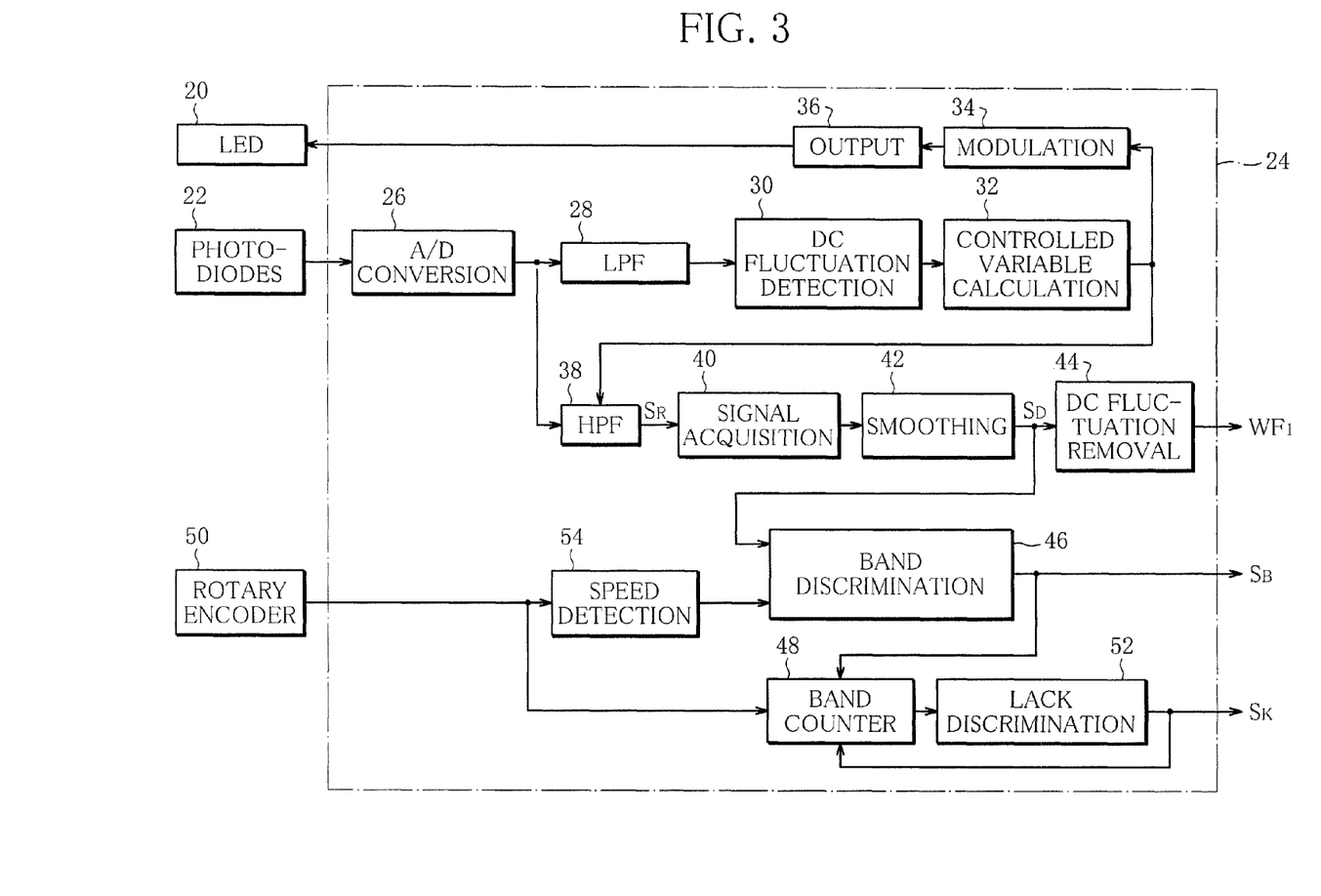
FIG. 3 is a block diagram illustrating functionality of a band detection board appearing in FIG. 1.

The detection signal from the photodiodes 22 is first converted to a digital signal in a section 26 and then passed through a low-pass filter 28. Subsequently, direct-current fluctuation components contained in the detection signal are detected in a section 30, and a controlled variable for the amount of light to be radiated from the LEDs 20 is calculated in a section 32 on the basis of the detected direct-current fluctuation components. Then, based on the calculated controlled variable for the light amount, a driving signal for driving the LEDs 20 is modulated in a section 34, and the modulated driving signal is supplied to the LEDs 20 via an output section 36. Accordingly, the LEDs 20 can radiate appropriately controlled light onto the target side (bands B and non-banded regions) of the web W.

The detection signal that has passed through the A/D conversion section 26 is also supplied to a section 40 via a high-pass filter 38, of which the gain for the received light is adjusted in accordance with the controlled variable obtained in the section 32. Consequently, the section 40 can obtain a detection signal that accurately indicates the reflection intensity of the detection light.

The section 40 acquires the detection signal $S_R$ at regular sampling intervals. The strength of the acquired detection signal $S_R$ varies greatly depending on the presence/absence of the band B.

Figure 4:
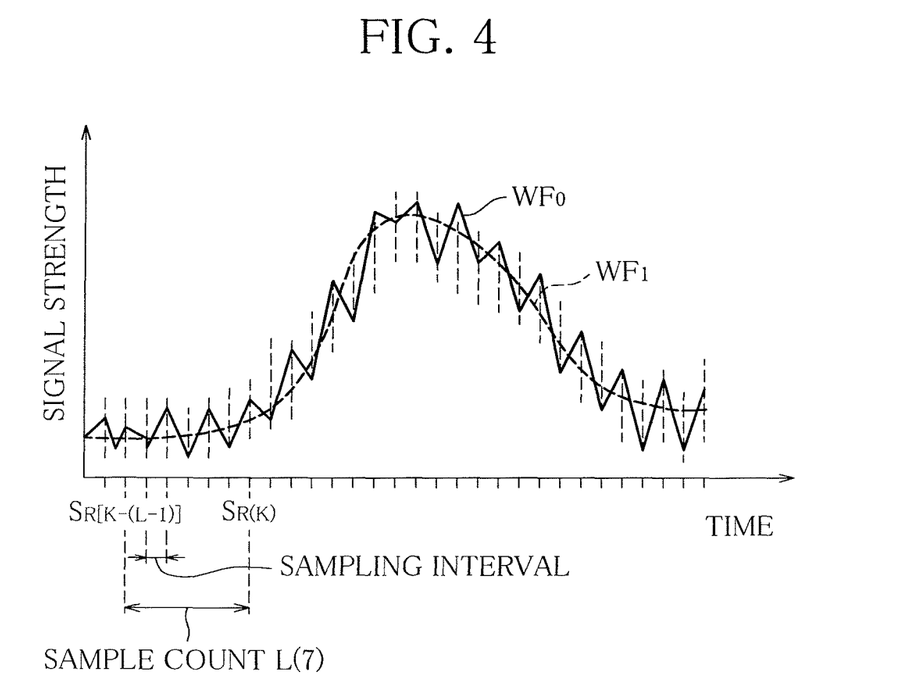
FIG. 4 is a graph showing an output waveform of a detection signal on the basis of which bands are detected.

Specifically, since the bands B are formed by applying the combustion inhibitor, the flatness of the bands B is higher than that of the non-banded regions. That is to say, the reflection intensity of the detection light reflected from the bands B is higher than that of the detection light reflected from the non-banded regions. Thus, when plotted along the axis of time, the acquired detection signal $S_R$ traces a waveform $WF_0$ corresponding to the bands B. However, since the detection signal $S_R$ fluctuates because of wrinkles, wavy deformation or the like of the web W as stated above, the waveform $WF_0$ is jagged as shown in FIG. 4.

The detection signal $S_R$ is supplied from the section 40 to a subsequent smoothing section 42, which performs a process of smoothing the detection signal $S_R$. Specifically, the smoothing section 42 successively calculates a moving average value of the detection signal $S_R$ according to the formula indicated below, and outputs the moving average value as a smoothed detection signal $S_D$ (moving average value calculation process).

$$S_{D(k)} = (S_{R(k)} + S_{R(k-1)} \cdots + S_{R[k-(L-1)]})/L$$

In the formula, k represents a sampling end number of the detection signal $S_R$ which is the target of moving average processing, and L represents the number of samples, or sample count. In this embodiment, the sample count is "7".

The detection signal $S_D$ obtained in this manner is supplied to a subsequent section 44, where the aforementioned direct-current fluctuation components are removed from the detection signal $S_D$. The processed detection signal $S_D$ is then output from the section 44 to a display device (not shown) and displayed at the display device as a waveform $WF_1$.

The waveform $WF_1$ is obtained by plotting the detection signal $S_D$ along the time axis and is smoother than the waveform $WF_0$ derived from the detection signal $S_R$, as shown in FIG. 4.

The detection signal $S_D$ is also supplied to a discrimination section 46 as a band discriminator, and based on the detection signal $S_D$, the discrimination section 46 detects the bands B on the web W (band discrimination process).

Figure 5:
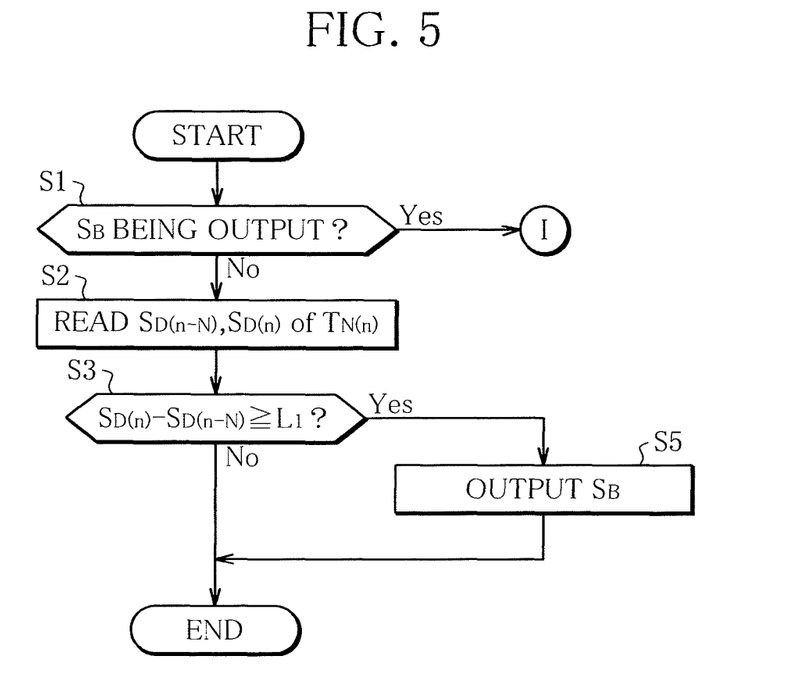
FIG. 5 is a flowchart showing part of a band discrimination procedure executed by a band discrimination section of the embodiment.
Figure 6:
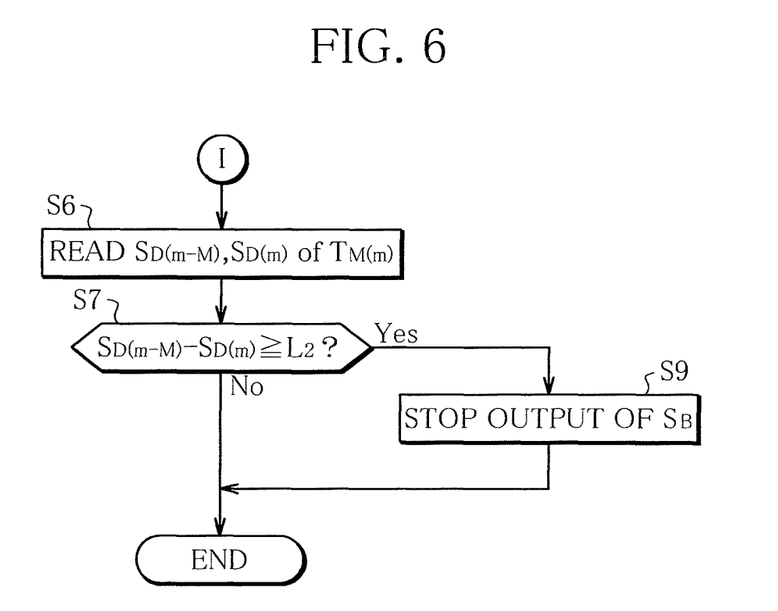
FIG. 6 is a flowchart showing the remaining part of the band discrimination procedure.

Specifically, each time the detection signal $S_D$ is detected, the discrimination section 46 executes a band discrimination procedure illustrated in FIGS. 5 and 6. In the following, the band discrimination procedure will be explained.

Assuming that the detection signal $S_{D(n)}$, by way of example, is supplied to the discrimination section 46, it is determined first in Step S1 whether a band signal $S_B$ is being output or not, and if the decision is "false" (N), Step S2 is executed. In Step S2, the detection signals $S_{D(n-N)}$ and $S_{D(n)}$ at the starting and ending points of a predetermined monitoring period $T_{N(n)}$ (see FIG. 7) are read. In this embodiment, "N" in the monitoring period $T_{N(n)}$ indicates that the monitoring period T is defined as an integral multiple N of the output cycle of the detection signal $S_D$, and "n" in $S_{D(n)}$ and $T_{N(n)}$ indicates the position of the detection signal $S_D$ and of the monitoring period $T_N$ with respect to the time axis, as seen from FIG. 7.

In Step S3, the determination indicated by the following formula is made:

$$S_{D(n)} - S_{D(n-N)} \geq L_1$$

In the formula, $L_1$ represents a rise discriminating level.

If the decision in Step S3 is "false", the succeeding detection signal $S_{D(n+1)}$ is supplied to the discrimination section 46, and the same process as described above is repeated from Step S1.

Steps S1 to S3 are repeatedly executed thereafter, and when the decision in Step S3 becomes "true" (Y), the band signal $S_B$ is output. That is, the band signal $S_B$ is output at the time the level difference between the detection signals $S_{D(n-N)}$ and $S_{D(n)}$ of a certain monitoring period $T_N$ becomes greater than or equal to the rise discriminating level $L_1$ (Step S5).

When Step S1 is executed after the band signal $S_B$ is output, the decision in Step S1 becomes "true", and therefore, the flow proceeds from Step S1 to Step S6 in FIG. 6. In this step, the detection signals $S_{D(m-M)}$ and $S_{D(m)}$ at the starting and ending points of a predetermined monitoring period $T_{M(m)}$ are read. "M" in the monitoring period $T_{M(m)}$ indicates that the monitoring period T is defined as an integral multiple M of the output cycle of the detection signal $S_D$, and "m" in $S_{D(m)}$ and $T_{M(m)}$ indicates the positions of the detection signal $S_D$ and monitoring period $T_M$ with respect to the time axis, as seen from FIG. 7, "n" and "m" being in the relationship: n<m.

In the following Step S7, the determination indicated by the following formula is made:

$$S_{D(m-M)} - S_{D(m)} \geq L_2$$

In the formula, $L_2$ indicates a fall discriminating level, and $L_1$ and $L_2$ are in the relationship: $L_1 \geq L_2$.

If the decision in Step S7 is "false", the succeeding detection signal $S_{D(m+1)}$ is supplied to the discrimination section 46 with the band signal $S_B$ being output, and the same process as described above is repeated from Step S1.

Steps S1, S6 and S7 are repeatedly executed thereafter, and when the decision in Step S7 becomes "true" (Y), the output of the band signal $S_B$ is stopped (Step S9). That is, the output of the band signal $S_6$ is stopped at the time the level difference between the detection signals $S_{D(m-M)}$ and $S_{D(m)}$ of a certain monitoring period $T_M$ becomes greater than or equal to the fall discriminating level $L_2$.

Figure 7:
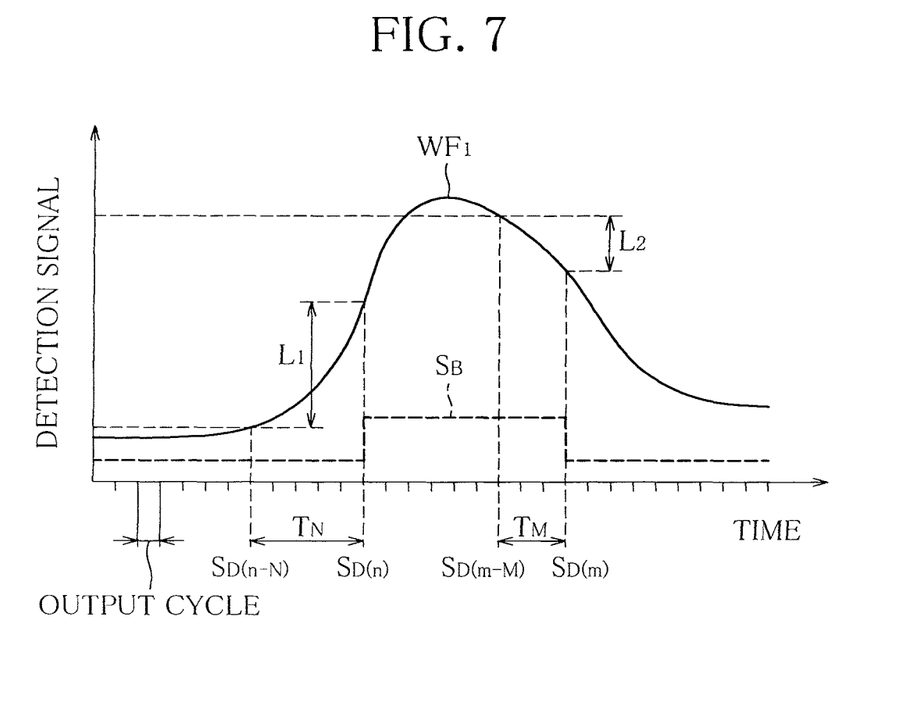
FIG. 7 is a graph showing a rise discriminating criterion and a fall discriminating criterion according to the embodiment, together with an output waveform of the detection signal.

As is clear from the above, the discrimination section 46 detects the presence/absence of the bands B not only on the basis of a rise discriminating criterion (monitoring period $T_N$ and rise discriminating level $L_1$) indicating a rate of rise of the detection signal $S_D$ but also on the basis of a fall discriminating criterion (monitoring period $T_M$ and fall discriminating level $L_2$) indicating a rate of fall of the detection signal $S_D$. Thus, even if the web W is wrinkled or wavily deformed as mentioned above, such wrinkles or wavy deformation scarcely affects the detection of the bands B, and not only the presence but effective width of the bands B can be detected with high accuracy. Needless to say, in place of the detection signal $S_D$, the detection signal $S_R$ may be directly used as the detection signal.

Also, to detect the bands B, near-infrared light is used as the detection light, and in addition, the photodiodes 22 are used in combination with the optical filter 23 for cutting off the visible light. Consequently, external light such as light from lighting equipment exerts no adverse influence on the detection of the bands B.

Further, since the angle between the optical axis of the LEDs 20 and the web W is set to 30 degrees or less, the detection light is efficiently reflected by the web W, so that the reflected detection light distinctively shows the presence/absence of the bands B on the web W.

The band detection sensor 10 of this embodiment can detect not only the bands B but also the lack of the bands B. The manner of how the lack of the bands B is detected will be explained below.

As illustrated in FIG. 3, the detection board 24 further includes a band lack discriminator which is constituted by a band counter 48, a rotary encoder 50, and a lack discrimination section 52. The rotary encoder 50 is attached to the feed roller of the aforementioned feed roller unit 16 as shown in FIG. 1, and supplies a pulse signal corresponding to a travel distance of the web W to the band counter 48.

Figure 8:
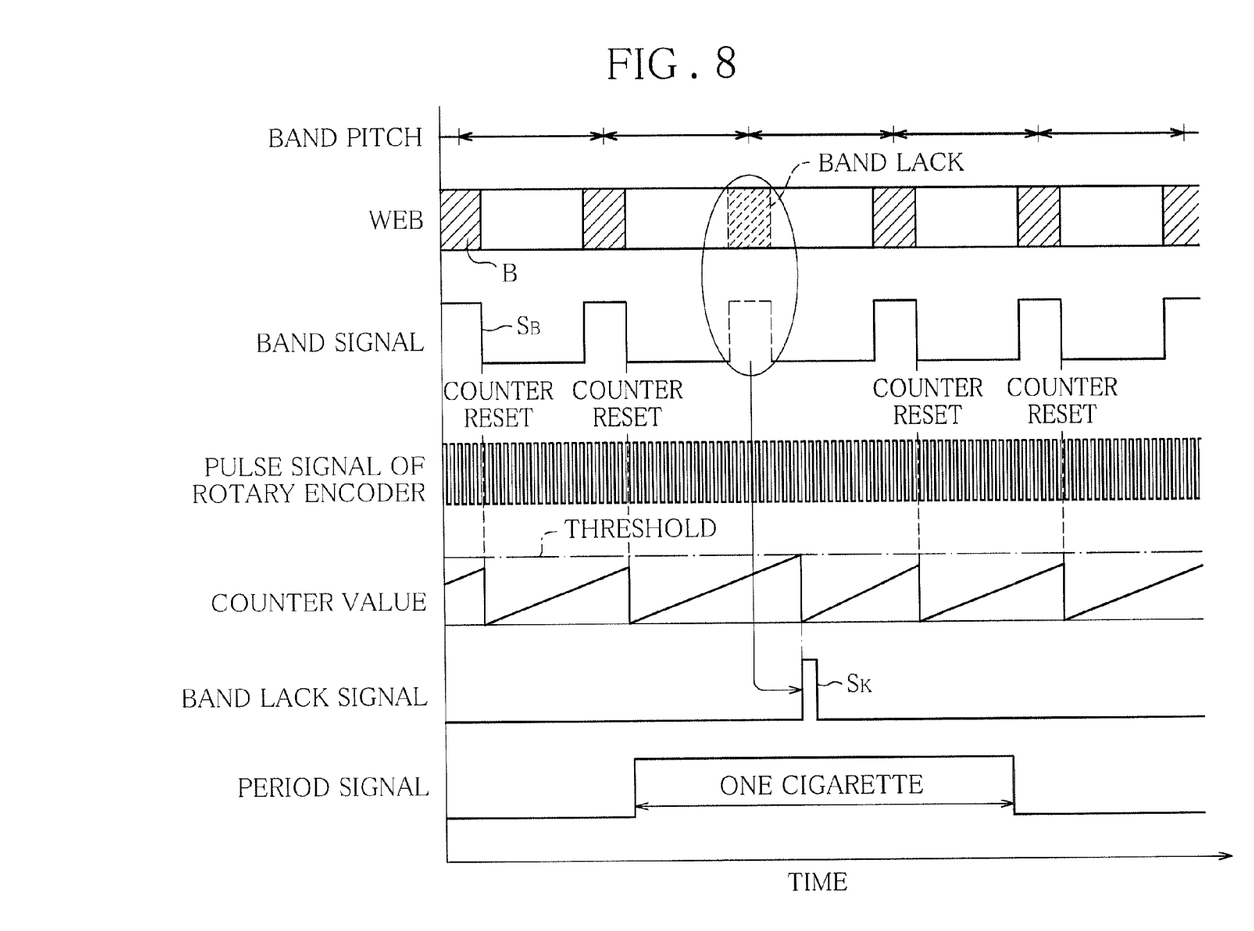
FIG. 8 is a chart illustrating functions of a band counter and lack discrimination section of a band lack discriminator.

The band counter 48 is also connected to the discrimination section 46, and operation of the band counter 48 is controlled by the start or stop of the output of the aforementioned band signal $S_B$. For example, the band counter 48 is reset each time the output of the band signal $S_B$ stops. In this case, as shown in FIG. 8, the band counter 48 is restarted each time the output of the band signal $S_B$ stops, and keeps incrementing its counter value until the output of the next band signal $S_B$ stops.

The band counter 48 supplies the counter value to the lack discrimination section 52 as shown in FIG. 3. The lack discrimination section 52 compares the counter value supplied from the band counter 48 with a threshold value, and if the counter value reaches the threshold value without being reset because of the lack of a band B, the lack discrimination section 52 outputs a band lack signal $S_K$ to outside, as shown in FIG. 8. Also, the band lack signal $S_K$ is fed back to the band counter 48 as a reset signal. The threshold value is set to a value such that it is greater than the counter value at all times if the bands B on the web W are spaced from each other with the fixed pitch.

With the above procedure for detecting the lack of the bands B, the counter value exceeds the threshold value only when a band B is lacking, whereby lack of the bands B can be reliably detected.

The present invention is not limited to the band detection sensor 10 of the foregoing embodiment and may be modified in various ways.

Figure 9:
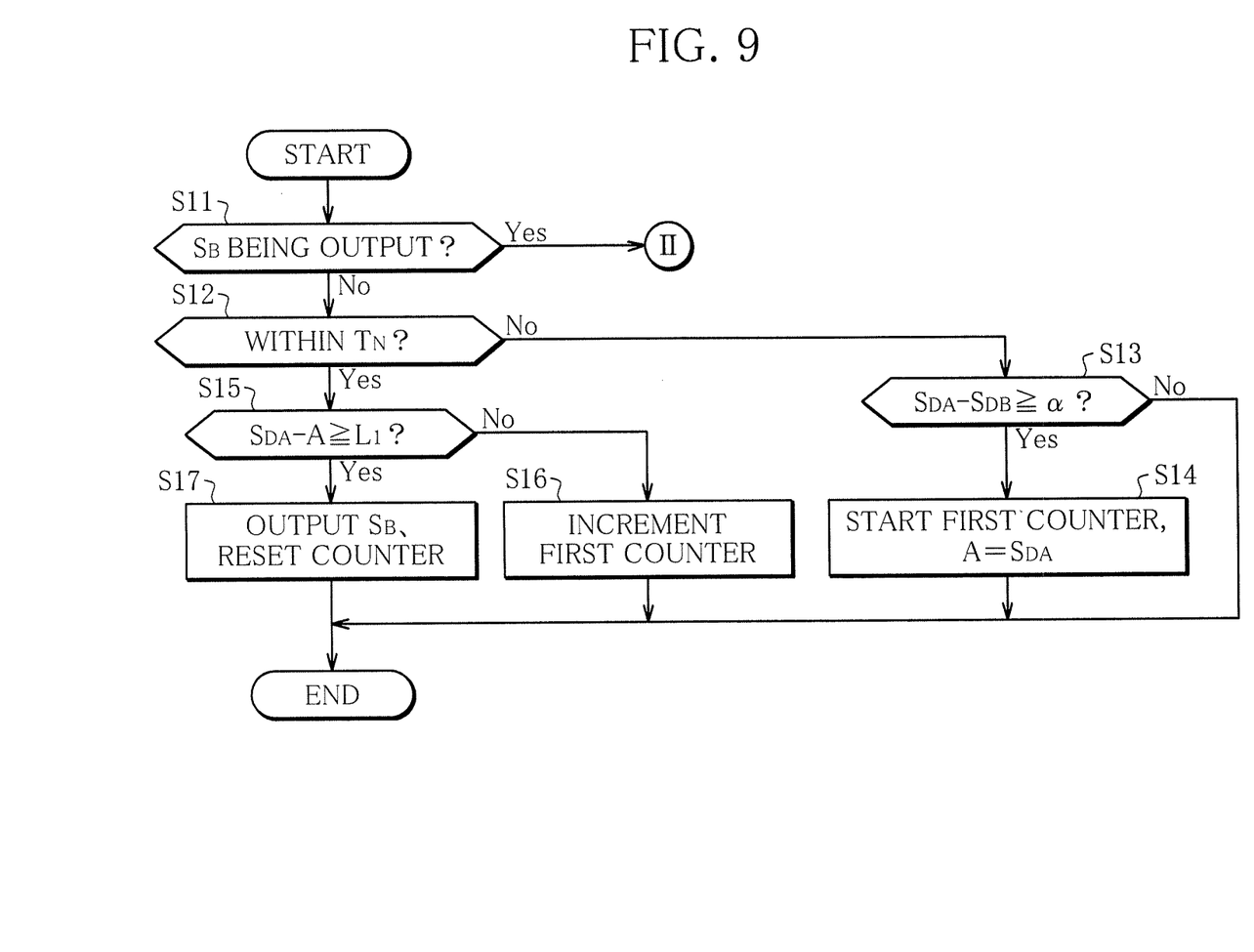
FIG. 9 is a flowchart showing part of a band discrimination procedure executed by a band discrimination section according to a modification.
Figure 10:
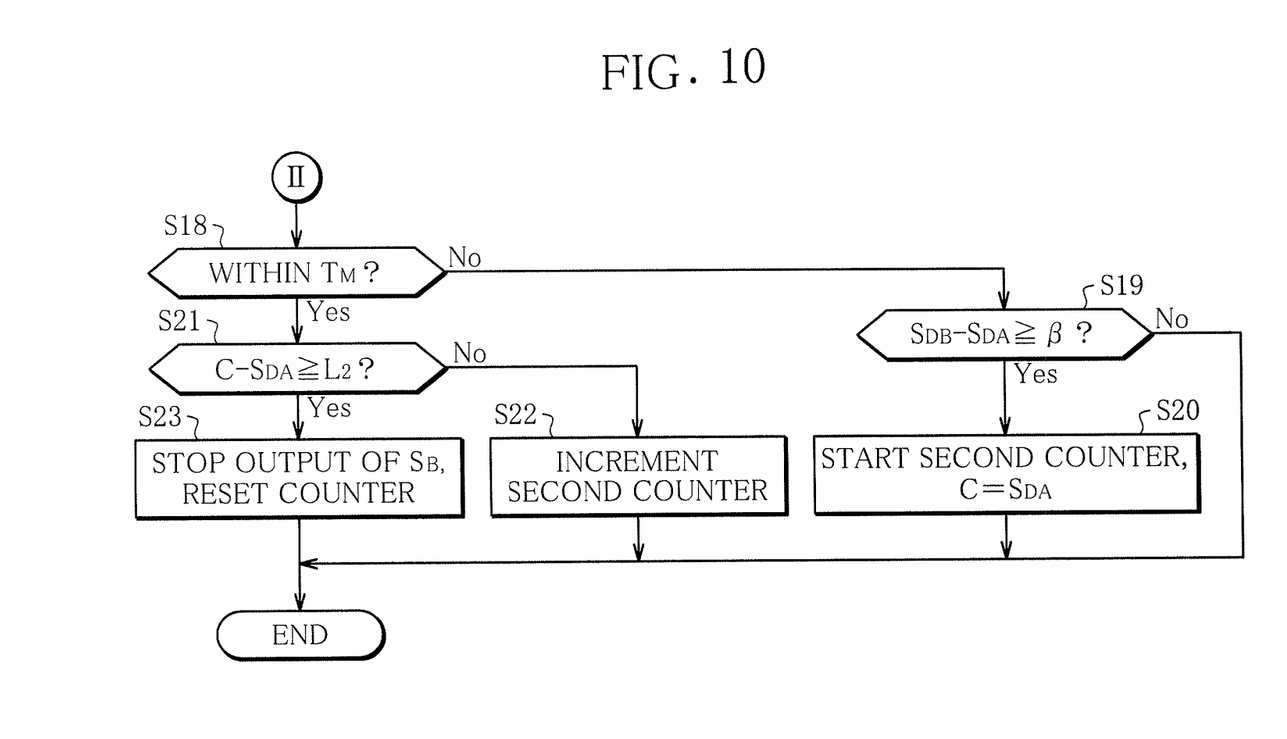
FIG. 10 is a flowchart showing the remaining part of the band discrimination procedure according to the modification.

For example, the discrimination section 46 may execute a band discrimination procedure shown in FIGS. 9 and 10, in place of the band discrimination procedure shown in FIGS. 5 and 6, to detect the bands B.

First, in Step S11 of FIG. 9, it is determined whether or not the band signal $S_B$ is being output, as in the aforementioned Step S1. If the decision is "false", it is determined whether or not a first counter for measuring the aforementioned monitoring period $T_N$ shows a value falling within $T_N$ (Step S12). If the decision in Step S12 is "false", the determination indicated by the following formula is made in Step S13:

$$S_{DA}-S_{DB} \geq \alpha$$

Figure 11:
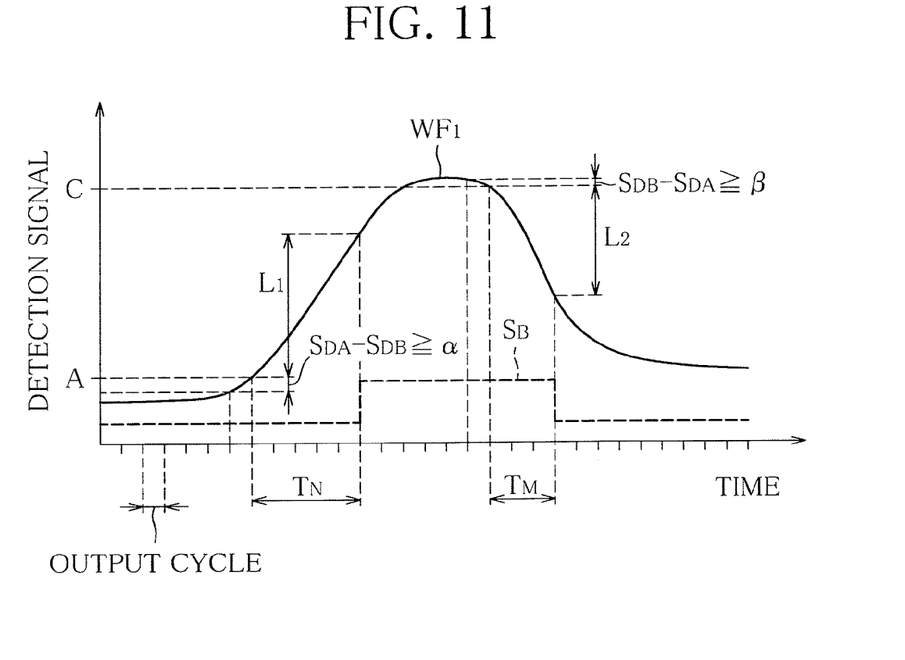
FIG. 11 is a graph showing a rise discriminating criterion and a fall discriminating criterion according to the modification, together with an output waveform of the detection signal.

In the formula, $S_{DA}$ and $S_{DB}$ are present and previous values, respectively, of the detection signal $S_D$ output from the aforementioned smoothing section 42, and as shown in FIG. 11, $\alpha$ is a desired threshold value indicating a change in rise of the waveform $WF_1$.

If the decision in Step S13 is "false", Steps S11 to S13 are repeatedly executed, and when the decision in Step S13 becomes "true", operation of the first counter is started and the detection signal $S_{DA}$ is substituted for a reference value A (Step S14).

Once Step S14 is executed, the decision in Step S12 executed subsequently becomes "true", and the determination indicated by the following formula is made in Step S15:

$$S_{DA}-A \geq L_1$$

As shown in FIG. 11, $L_1$ is the aforementioned rise discriminating level.

If the decision in Step S15 is "false", the first counter counts up, that is, its counter value is incremented (Step S16). Consequently, Step S15 is repeatedly executed as long as the decision in Step S12 remains "true", that is, until the monitoring period $T_N$ expires.

If the decision in Step S15 becomes "true", the band signal $S_B$ is output (Step S17). Also, in Step S17, the value of the first counter is reset.

When Step S11 is executed after the band signal $S_B$ is output, the decision in Step S11 becomes "true", and accordingly, in Step S18 in FIG. 10, it is determined whether or not a second counter for measuring the monitoring period $T_M$ shows a value falling within $T_M$. If the decision in Step S18 is "false", the determination indicated by the following formula is made in Step S19:

$$S_{DB}-S_{DA} \geq \beta$$

As shown in FIG. 11, $\beta$ is a threshold value indicating a change in fall of the waveform $WF_1$.

If the decision in Step S19 is "false", Steps S18 and S19 are repeatedly executed, and when the decision in Step S19 becomes "true", operation of the second counter is started and the detection signal $S_{DA}$ is substituted for a reference value C (Step S20).

Once Step S20 is executed, the decision in Step S18 executed subsequently becomes "true", and the determination indicated by the following formula is made in Step S21:

$$C-S_{DA} \geq L_2$$

As seen from FIG. 11, $L_2$ is the aforementioned fall discriminating level.

If the decision in Step S21 is "false", the second counter counts up, that is, its counter value is incremented (Step S22). Consequently, Step S21 is repeatedly executed as long as the decision in Step S18 remains "true", that is, until the monitoring period $T_M$ expires.

If the decision in Step S21 becomes "true", the output of the band signal $S_B$ is stopped (Step S23). Further, in Step S23, the value of the second counter is reset.

Also with the above band discrimination procedure shown in FIGS. 9 and 10, the bands B can be accurately detected irrespective of wrinkles or wavy deformation of the web W, as with the band discrimination procedure shown in FIGS. 5 and 6.

The monitoring periods $T_N$ and $T_M$ may each be defined as a count of pulses of the pulse signal output from the rotary encoder 50, instead of a number of output cycles of the detection signal $S_D$.

Also, as shown in FIG. 3, the detection board 24 may further include a speed detection section 54 connected to the rotary encoder 50. The speed detection section 54 detects a traveling speed of the web W on the basis of the pulse signal from the rotary encoder 50, and supplies the detected traveling speed to the discrimination section 46.

On the other hand, the discrimination section 46 varies the length of the monitoring period in accordance with the traveling speed of the web W so that the length of the web W delivered within the monitoring period may be constant. In this case, even if the traveling speed of the web W is changed, each discriminating criterion is represented by two positions on the web W spaced from each other in the longitudinal direction of the web W and falling within a predetermined distance and a level difference between the detection signals obtained at these two positions. This makes it possible to set a discriminating criterion whose monitoring period is represented in terms of distance and independent of the traveling speed of the web W.

Further, the band detection sensor 10 of the present invention can be applied not only to detection of the bands on the web W used in the manufacture of cigarettes but also to detection of bands formed on a variety of webs.

In cases where the type of web W used for making cigarettes or the lot is changed from one to another, the degree of reflection of the detection light from the web may change and the value of the detection signal may increase or decrease as a whole. Even in such cases, the band detection sensor of the present invention can be used without the need to change the settings of the threshold values and the like in relation to the web or lot.

REFERENCE SIGNS LIST

- 10: band detection sensor
- 20: LED (light emitter)
- 22: photodiode (light receiver)
- 23: optical filter
- 24: detection board
- 26: A/D conversion section
- 28: low-pass filter
- 34: modulation section
- 38: high-pass filter
- 46: band discrimination section (band discriminator)
- 48: band counter
- 50: rotary encoder
- 52: lack discrimination section
- 54: speed detection section
- $S_B$: band signal
- $S_N$: band lack signal
- W: web The invention claimed:

1. A band detection sensor for detecting bands arranged on one side of a web and spaced from each other in a longitudinal direction of the web, comprising:
    a light emitter arranged at a location along a travel path of the web and configured to radiate detection light onto the one side of the web;
    a light receiver arranged at a location along the travel path at a distance from the light emitter along the travel path, the light receiver being configured to receive the detection light reflected by the web and output a detection signal corresponding to intensity of the received detection light; and
    a band discriminator configured to discriminate the bands on the web on the basis of the detection signal from the light receiver,
    wherein the band discriminator includes a rise discriminating criterion indicating a rate of rise of the detection signal and generates a band signal indicative of presence of the band when change of the detection signal fulfills the rise discriminating criterion.

2. The band detection sensor according to claim 1, wherein the detection light is invisible light.

3. The band detection sensor according to claim 1, wherein an angle between an optical axis of the light emitter and the one side of the web is 30 degrees of less.

4. The band detection sensor according to claim 1, wherein the rise discriminating criterion is represented by two positions on the web spaced from each other in the longitudinal direction of the web and a level difference between the detection signals obtained at the two positions.

5. The band detection sensor according to claim 1, wherein the band discriminator discriminates the bands on the web on the basis of a moving average value calculated from a predetermined number of the detection signals and the rise discriminating criterion.

6. The band detection sensor according to claim 1, wherein the band discriminator further includes a fall discriminating criterion indicating a rate of fall of the detection signal.

7. The band detection sensor according to claim 1, wherein:
    the bands are arranged on the web with a fixed pitch, the band detection sensor further comprises a band lack discriminator configured to discriminate lack of the band, and
    the band lack discriminator outputs a band lack signal when a predetermined threshold value is reached by a counter value which is incremented while being reset each time the band signal is output or output of the band signal is stopped.

8. The band detection sensor according to claim 1, wherein the web is a cigarette wrapper web for wrapping shredded tobacco material therein, and the bands are formed by applying a combustion inhibitor in liquid form.

9. A band detection method for detecting bands arranged on one side of a web and spaced from each other in a longitudinal direction of the web, comprising:
    a radiation process of radiating detection light onto the one side of the web while the web is traveling along a travel path;
    an output process of receiving the detection light reflected by the web and outputting a detection signal corresponding to intensity of the received detection light; and
    a band discrimination process of discriminating the bands on the web on the basis of the detection signal output in the output process,
    wherein the band discrimination process includes using a rise discriminating criterion indicating a rate of rise of the detection signal and generating a band signal indicative of presence of the band when change of the detection signal fulfills the rise discriminating criterion.

* * * * *